(12) United States Patent
Hayashi et al.

(10) Patent No.: US 10,732,137 B2
(45) Date of Patent: Aug. 4, 2020

(54) ELECTROCHEMICAL MEASUREMENT METHOD, ELECTROCHEMICAL MEASUREMENT APPARATUS AND TRANSDUCER

(71) Applicants: JAPAN AVIATION ELECTRONICS INDUSTRY, LIMITED, Tokyo (JP); TOHOKU UNIVERSITY, Miyagi (JP)

(72) Inventors: Hiroyuki Hayashi, Tokyo (JP); Ryota Kunikata, Tokyo (JP); Atsushi Suda, Tokyo (JP); Kosuke Ino, Miyagi (JP); Kumi Inoue, Miyagi (JP); Tomokazu Matsue, Miyagi (JP)

(73) Assignees: JAPAN AVIATION ELECTRONICS INDUSTRY, LIMITED, Tokyo (JP); TOHOKU UNIVERSITY, Miyagi (JP)

( * ) Notice: Subject to any disclaimer, the term of this patent is extended or adjusted under 35 U.S.C. 154(b) by 22 days.

(21) Appl. No.: 16/095,531

(22) PCT Filed: Dec. 13, 2016

(86) PCT No.: PCT/JP2016/087029
§ 371 (c)(1),
(2) Date: Oct. 22, 2018

(87) PCT Pub. No.: WO2017/187661
PCT Pub. Date: Nov. 2, 2017

(65) Prior Publication Data
US 2019/0086356 A1    Mar. 21, 2019

(30) Foreign Application Priority Data
Apr. 26, 2016   (JP) ................................ 2016-087924

(51) Int. Cl.
*G01N 27/30*    (2006.01)
*G01N 27/403*   (2006.01)
(Continued)

(52) U.S. Cl.
CPC .......... *G01N 27/30* (2013.01); *G01N 27/403* (2013.01); *G01N 27/416* (2013.01); *G01N 33/48735* (2013.01)

(58) Field of Classification Search
CPC .............. G01N 27/327; G01N 27/403; G01N 33/4836; C12Q 1/02; C12Q 1/025; C12Q 1/04
See application file for complete search history.

(56) References Cited

U.S. PATENT DOCUMENTS

| | | | |
|---|---|---|---|
| RE37,977 E * | 2/2003 | Sugihara ................ | C12M 41/46 204/403.01 |
| 2004/0045839 A1* | 3/2004 | Thewes .................. | C12Q 1/001 205/777.5 |

(Continued)

FOREIGN PATENT DOCUMENTS

| | | |
|---|---|---|
| JP | 2005-148058 A | 6/2005 |
| JP | 2010-014558 A | 1/2010 |

(Continued)

OTHER PUBLICATIONS

USPTO STIC English language translation of the Description section of JP 04-204244 A, patent published on Jul. 24, 1992 (Year: 1992).*

(Continued)

*Primary Examiner* — Alexander S Noguerola
(74) *Attorney, Agent, or Firm* — Greenblum & Bernstein, P.L.C.

(57) ABSTRACT

An electrochemical measurement method is provided in which a working electrode and a counter electrode are provided in an electrolytic solution containing the measurement target and a measuring voltage is applied between the working electrode and the counter electrode to measure a current flowing between the working electrode and the counter electrode in proportion to the amount of the mea- (Continued)

surement target. A measurement target eliminating thin-wire electrode made of thin wire stretched in such a shape that extends from one point on the bottom into space in the electrolytic solution well and back to another point on the bottom is provided. The electrochemical measurement method includes: eliminating the measurement target by applying an eliminating voltage having the same polarity as the measuring voltage between the measurement target eliminating thin-wire electrode and the counter electrode; and diffusing a new measurement target after stopping the application of the eliminating voltage.

16 Claims, 11 Drawing Sheets

(51) Int. Cl.
*G01N 33/487* (2006.01)
*G01N 27/416* (2006.01)

(56) References Cited

U.S. PATENT DOCUMENTS

| | | | | |
|---|---|---|---|---|
| 2004/0110277 | A1* | 6/2004 | Maeda | G01N 33/5438 435/287.2 |
| 2004/0152067 | A1* | 8/2004 | Wang | G01N 33/5005 435/4 |
| 2004/0214312 | A1* | 10/2004 | Tyvoll | G01N 33/48728 435/288.4 |
| 2009/0281410 | A1* | 11/2009 | Ushio | G01N 33/48728 600/395 |
| 2010/0243479 | A1 | 9/2010 | Choi et al. | |
| 2013/0045536 | A1* | 2/2013 | Nakatani | C12M 25/14 435/398 |
| 2015/0260675 | A1* | 9/2015 | Nakatani | G01N 33/48728 204/403.01 |
| 2017/0336384 | A1 | 11/2017 | Ino et al. | |
| 2018/0372676 | A1 | 12/2018 | Kunikata et al. | |

FOREIGN PATENT DOCUMENTS

| | | |
|---|---|---|
| JP | 2010-227089 A | 10/2010 |
| JP | 2013-092437 A | 5/2013 |
| WO | 2014/073195 A1 | 5/2014 |
| WO | 2015/151395 A1 | 10/2015 |

OTHER PUBLICATIONS

EPO English language translation of the Description section of JP 2010-121948 A, patent published Jun. 3, 2010 (Year: 2010).*
EPO English language translation of the Description section of JP 2013-3094168 A, patent published May 20, 2013 (Year: 2013).*
Inoue et al., "LSI-based amperometric sensor for bio-imaging and multi-point biosensing," Lab Chip, 2012, 12, 3481-3490 (Year: 2012).*
Ino et al., "Electrochemical Device with Interdigitated Ring Array Electrodes for Investigating the Relationship between Cardiomyocyte Differentiation from Embryonic Stem Cells and Alkaline Phosphatase Activity", Electrochemistry, vol. 81, No. 9, 2013, pp. 682-687.
Kanno et al., "Simulation Analysis of Positional Relationship between Embryoid Bodies and Sensors on an LSI-based Amperometric Device for Electrochemical Imaging of Alkaline Phosphatase Activity", Analytical Sciences, vol. 31, Jul. 10, 2015, pp. 715-719.
Sen et al., "LSI-based amperometric sensor for real-time monitoring of embryoid bodies", Biosensors and Bioelectronics, vol. 48, 2013, pp. 12-18.
U.S. Appl. No. 15/776,195 to Hiroyuki Hayashi et al., filed May 15, 2018.
International Search Report issued in International Bureau of WIPO Patent Application No. PCT/JP2016/087029, dated Feb. 28, 2017.

* cited by examiner

ELECTROCHEMICAL MEASUREMENT METHOD, ELECTROCHEMICAL MEASUREMENT APPARATUS AND TRANSDUCER

TECHNICAL FIELD

The present invention relates to an electrochemical measurement method, an electrochemical measurement apparatus, and a transducer used for electrochemical measurement for measuring chemical substances (chemical reaction products) derived from cells, cell aggregates, pieces of tissue and other biological specimens, and non-biological specimens containing biologically-relevant substances (which are collectively simply referred to as "biological specimens" hereinafter).

BACKGROUND ART

Quantifying a substance produced by a chemical reaction that occurs in biological specimens such as cells, cell aggregates, and pieces of tissue is a technique required for viability assay, functional assay and the like of biological specimens in fields such as medical and drug discovery. One method for quantifying a chemical reaction product released from a biological specimen is electrochemical measurement. For example, the progress of stem cell differentiation is monitored using electrochemical measurement in Non-patent literature 1.

Electrochemical measurement is a method in which an oxidization or reduction reaction is caused to a measurement target in an electrolytic solution in which two or more electrodes connected to an external power source are inserted, by removing electrons from the measurement target or supplying electrons to the measurement target through electrodes, while at the same time a current flowing between the electrodes is measured to determine whether an oxidation-reduction reaction has occurred, that is, to detect the presence or absence of the measurement target.

A typical electrochemical measurement apparatus includes a working electrode, which supplies or receives electrons to or from a measurement target to cause an oxidation-reduction reaction, a counter electrode, which is connected to the working electrode through an external power source and compensates for electron transfer occurring at the working electrode, an electrolytic solution, which enables transfer of electrons through ions in a measurement system and makes the entire measurement system a closed circuit, and a reference electrode for providing a reference for voltage.

In Non-patent literature 1, alkaline phosphatase (ALP), which is an undifferentiation marker and exists in the cell membranes of embryonic stem (ES) cells, is indirectly measured by electrochemical measurement for an embryoid body (EB) which is an aggregate of ES cells produced from ES cells of a mouse.

The reaction in which a stem cell whose function is yet to be determined changes to a somatic cell whose function is determined is commonly referred to as differentiation and a substance that indicates that differentiation has not occurred is referred to as an undifferentiation marker.

ALP is a cell undifferentiation marker and also has the property of hydrolyzing a phosphoric ester compound under alkaline conditions. For example, ALP acts as an enzyme in a reaction that changes p-aminophenyl phosphate (PAPP), which is a phosphoric ester compound, into p-aminophenol (PAP). PAP produced by the enzymatic reaction is a substance that is electrochemically active and is oxidized to p-quinone imine (PQI) by application of a voltage to the working electrode using the reference electrode as a reference. Specifically, the presence of ALP is detected as a current value in electrochemical measurement through two reactions of an enzymatic reaction and an oxidation-reduction reaction.

In Non-patent literature 1, a multielectrode amperometric device in which 20×20=400 working electrodes with a diameter of $\phi 40$ μm are provided in an array with a pitch of 250 μm is used for measurement. The device two-dimensionally images reactions in biological specimens of several to several hundred micrometers over time by using electrode current values acquired from the 400 electrodes.

PRIOR ART LITERATURE

Non-Patent Literature

Non-patent literature 1: M. Sen, et al., "Biosensors and Bioelectronics", 2013, Vol. 48, pp. 12-18

SUMMARY OT THE INVENTION

Problem to be Solved by the Invention

The above-described measurement in Non-patent literature 1 is performed in the following process, which is illustrated in FIG. 1 where the horizontal axis represents time.

Mouse EB is introduced in an electrolytic solution containing $4.7 \times 10^{-3}$ mol/L of PAPP.

Enzymatic reaction starts immediately after the introduction and PAPP changes to PAP by ALP in cell membranes.

PAP diffuses from the surface of the EB to regions near the electrodes and reaches the surfaces of the electrodes.

A voltage is applied to the electrodes after the diffusion is stabilized.

PAP changes to PQI.

Interelectrode current values are acquired.

In FIG. 1, the time A from the start of the enzymatic reaction after the introduction of the EB in the electrolytic solution to the application of the voltage is provided by taking into consideration the time required for the PAP concentration distribution in the electrolytic solution to stabilize after the start of diffusion of PAP from the surface of the EB, and the time B from the voltage application to the current value acquisition is provided by taking into consideration the time required for changes in the PAP concentration distribution near the electrodes to be stabilized by an oxidation-reduction reaction which occurs on the electrodes.

In measurement of ALP activity in EB that follows such a process, uncertainty of the measurement can arise.

For example, in the case where multiple EBs are concurrently measured, the EBs contact PAPP at different timings when the EBs are placed on the electrodes in an array with a pipette or the like in multiple batches. Accordingly, the time A from the start of an enzymatic reaction to voltage application differs from EB to EB and the PAP concentration distributions around the EBs and current values vary even if all of the EBs have activities (PAP release rates per unit time) similar to one another. That is, both of a difference due to different levels of ALP activities of the EBs and a difference due to the lengths of the time A from the start of the enzymatic reaction to the voltage application appear in measured current values.

Even if multiple EBs are concurrently introduced in a PAPP solution, it may be difficult to compare a result of measurement on a group of EBs performed at a certain time with a result of measurement on the group of EBs performed at a different time because of reasons such as a difference in liquid fluctuations due to, for example, a manner in which an operator has introduced the EBs.

An object of the present invention is to provide an electrochemical measurement method, an electrochemical measurement apparatus and a transducer used in electrochemical measurement that are capable of making measurement conditions uniform among a plurality of repetitions of measurement and among a plurality of samples measured at a time, thus enabling accurate measurement and accurate comparison among results of measurement in the plurality of repetitions and among results of measurement performed on the plurality of samples at a time.

Means to Solve the Problems

The present invention provides an electrochemical measurement method in which a working electrode that supplies or receives electrons to or from a measurement target to cause an oxidation-reduction reaction and a counter electrode connected to the working electrode through an external power source are provided in an electrolytic solution containing the measurement target, and a measuring voltage is applied between the working electrode and the counter electrode to measure a current flowing between the working electrode and the counter electrode in proportion to the amount of the measurement target, wherein the working electrode is provided at a bottom of an electrolytic solution well containing the electrolytic solution; and a measurement target eliminating thin-wire electrode is provided on the bottom, the measurement target eliminating thin-wire electrode being made of thin wire stretched in such a shape that extends from one point on the bottom upward into space in the electrolytic solution well and back to another point on the bottom, the electrochemical measurement method performs: a measurement target elimination step of eliminating the measurement target by applying an eliminating voltage having the same polarity as the measuring voltage between the measurement target eliminating thin-wire electrode and the counter electrode to oxidize or reduce the measurement target; a measurement target diffusion step of diffusing a new measurement target after stopping the application of the eliminating voltage; and an electrochemical measurement step of measuring the current by applying the measuring voltage between the working electrode and the counter electrode after the new measurement target is diffused.

The present invention further provides an electrochemical measurement apparatus comprising an electrolytic solution well configured to contain an electrolytic solution and a biological specimen that produces a measurement target in the electrolytic solution, a working electrode that is provided at a bottom of the electrolytic solution well and causes an oxidation-reduction reaction by supplying or receiving electrons to or from the measurement target, a counter electrode provided in the electrolytic solution well, a measuring voltage applying means for applying a measuring voltage between the working electrode and the counter electrode, and a current measuring means for measuring a current flowing between the working electrode and the counter electrode in proportion to the amount of the measurement target while the measuring voltage is being applied, wherein a measurement target eliminating thin-wire electrode made of thin wire stretched in such a shape that extends from one point on the bottom upward into space in the electrolytic solution well and back to another point on the bottom is provided on the bottom, the measurement target eliminating thin-wire electrode causing an oxidation-reduction reaction by supplying or receiving electrons to or from the measurement target; and the electrochemical measurement apparatus comprises an eliminating voltage applying means for applying an eliminating voltage that has the same polarity as the measuring voltage between the measurement target eliminating thin-wire electrode and the counter electrode while the measuring voltage is not being applied between the working electrode and the counter electrode.

The present invention further provides a transducer comprising an electrolytic solution well that can contain an electrolytic solution and a biological specimen immersed in the electrolytic solution, the electrolytic solution well being mounted on an LSI chip, the transducer being used for electrochemical measurement of a measurement target produced from the biological specimen, wherein first electrodes arranged in an array and provided in the LSI chip are located in a sensor region defined on a bottom of the electrolytic solution well; a second electrode made of thin wire is provided on the sensor region; and the second electrode is stretched in such a shape that extends from one point in the sensor region upward into space in the electrolytic solution well and back to another point in the sensor region.

Effects of the Invention

The electrochemical measurement method according to the present invention eliminates a measurement target produced and diffused in an electrolytic solution, then produces and diffuses a measurement target again and performs measurement, and an electrochemical measurement apparatus according to the present invention is capable of such measurement. Therefore, the electrochemical measurement method and the electrochemical measurement apparatus according to the present invention are capable of making conditions for production and diffusion of measurement targets uniform, that is, capable of making measurement conditions uniform, thereby enabling accurate measurement.

Consequently, results of measurement can be accurately compared with one another among repetitions of the measurement and among a plurality of samples (biological specimens) on which the measurement is performed at a time.

Further, the transducer according to the present invention is suitable for use in such electrochemical measurement.

DETAILED DESCRIPTION OF THE EMBODIMENTS

Figure 1:
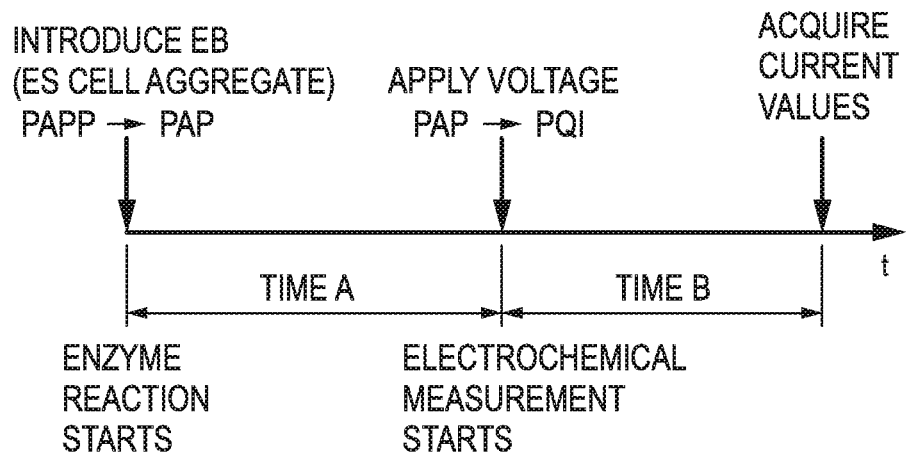
FIG. 1 is a chart illustrating an example of a conventional measurement process of electrochemical measurement.

Results of a numerical analysis by a finite element method will be described first using measurement of ALP activity of mouse EBs as an example. COMSOL Multiphysics Ver. 4.4 was used as numerical analysis software. Analytical model forms and boundary conditions will be described below.

<Analytical Model Forms>

An analytic space of 2.3 mm×2.3 mm×1.3 mm was provided and ϕ40-μm-diameter electrodes (working electrodes) were disposed in an array on the bottom of the analytic space.

An origin was set at the center of the bottom of the analytic space of 2.3 mm×2.3 mm, 8×8=64 electrodes were placed with a pitch of 250 μm so that the center of the entire electrode array coincided with the center of the bottom of the analytic space. A spherical object that models an EB with a diameter of ϕ300 μm was placed so that the center of the EB was above the electrode in the fifth column of the fourth row near the center of the electrode array. The distance between the spherical object and the electrode located immediately below the spherical object was chosen to be 3 μm by taking into consideration the ease of cutting an analytic mesh.

<Boundary Conditions>

A substrate PAPP with a concentration of $4.7\times10^{-3}$ mol/L was set in the analytic space as the initial value of the concentration in the space and the four walls and ceiling of the analytic space were set as open boundaries where the concentration outside the analytic space was $4.7\times10^{-3}$ mol/L. The surface of the EB (the surface of the spherical object) was set as a boundary through which PAP was released depending on the concentration of PAPP near the surface in accordance with the Michaelis-Menten equation (1) given below, resulting in an enzymatic reaction model.

[Formula 1]

$$v = \frac{V_{max}[S]}{K_m + [S]} \quad (1)$$

V: PAP release rate [mol/s]

[S]: Substrate PAPP concentration ($4.7\times10^{-3}$ mol/L)

$V_{max}$: Rate of reaction at the maximum PAPP concentration ($3.33\times10^{-12}$ mol/s)

$K_m$: Michaelis-Menten constant ($1.7\times10^{-3}$ mol/L)

In order to express an oxidation-reduction reaction of PAP, the PAP concentration was set to 0 during voltage application on the electrodes and a current value was calculated from the PAP concentration gradient. The current value is proportional to the concentration gradient in the direction perpendicular to the electrodes and follows equation (2).

[Formula 2]

$$i = nFD\frac{dC(x, y, z)}{dz} \quad (2)$$

i: Current density [A/m²] at an arbitrary point (x, y, z) on the electrodes

C: PAP concentration [mol] at the arbitrary point (x, y, z)

z: Component perpendicular to the electrodes x, y: Components horizontal to the electrodes F: Faraday constant (96485 C/mol)

D: Diffusion coefficient of redox species PAP ($6.47\times10^{-10}$ m²/s)

n: The number of reaction electrons (n=2)

Note that in order to evaluate the influence of the PAP concentration distribution in a visually clear manner, current values of seven electrodes (seven electrodes along the Y axis) in the same column on which the EB was placed among the 64 electrodes were used for the evaluation.

Figure 2:
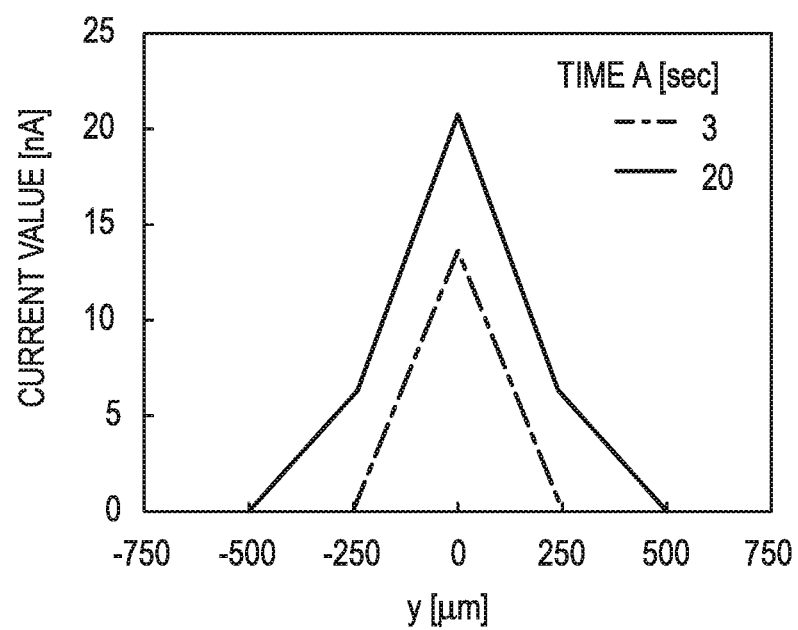
FIG. 2 is a graph illustrating differences in calculated current values that arises due to differences in time A of an enzymatic reaction in the electrochemical measurement illustrated in FIG. 1.

First, according to the process illustrated in FIG. 1, current values when the time A from the start of an enzymatic reaction to voltage application is 3 seconds and the time B from the voltage application to acquisition of the current values was 0.1 seconds and current values when the time A is 20 seconds and the time B is 0.1 seconds were calculated. The results are illustrated in FIG. 2. As illustrated in FIG. 2, the differences in time A from the start of the enzymatic reaction to the voltage application appeared as differences in the current values. Note that in FIG. 2, the position of the electrode located immediately below the EB is y=0 μm and current values from the electrode located immediately below the EB, three electrodes located on one side of the electrode, and three electrodes located on the other side of the electrode are plotted (the same applies to graphs in FIGS. 8 to 10, which will be described later).

The present invention performs a measurement target elimination step of eliminating a measurement target by providing a measurement target eliminating electrode in an electrolytic solution and applying an eliminating voltage of the same polarity as a measuring voltage between the measurement target eliminating electrode and a counter electrode to oxidize or reduce the measurement target, a measurement target diffusion step of diffusing a new measurement target after stopping the application of the eliminating voltage, and an electrochemical measurement step of measuring a current by applying the measuring voltage between working electrodes and the counter electrode after diffusing the new measurement target. Two configurations of the measurement target eliminating electrodes (configurations 1 and 2) used in the numerical analysis will be described below.

Configuration 1: Measurement target eliminating thin-wire electrodes having the same polarity as working electrodes are provided on the bottom on which the working electrodes are disposed (analytic space bottom). FIGS. 3, 4, 5A and 5B illustrate an arrangement and a configuration of the measurement target eliminating thin-wire electrodes. In FIGS. 3, 4, 5A and 5B, reference numeral 11 indicates ϕ40-μm working electrodes and reference numeral 21 indicates the measurement target eliminating thin-wire electrodes. Reference numeral 31 indicates a ϕ300-μm EB. The EB 31 is located immediately above the working electrode 11.

Each of the measurement target eliminating thin-wire electrodes 21 was made of a 33-μm-thick thin line (wire) stretched in an inverted U-shape extending from one point on the bottom 10 upward into space (in the Z direction) and back to another point on the bottom 10. The distance between the legs of the inverted U was 120 μm and the height of the center of the thin line of the inverted U from the bottom 10 was 300 μm.

Figure 4:
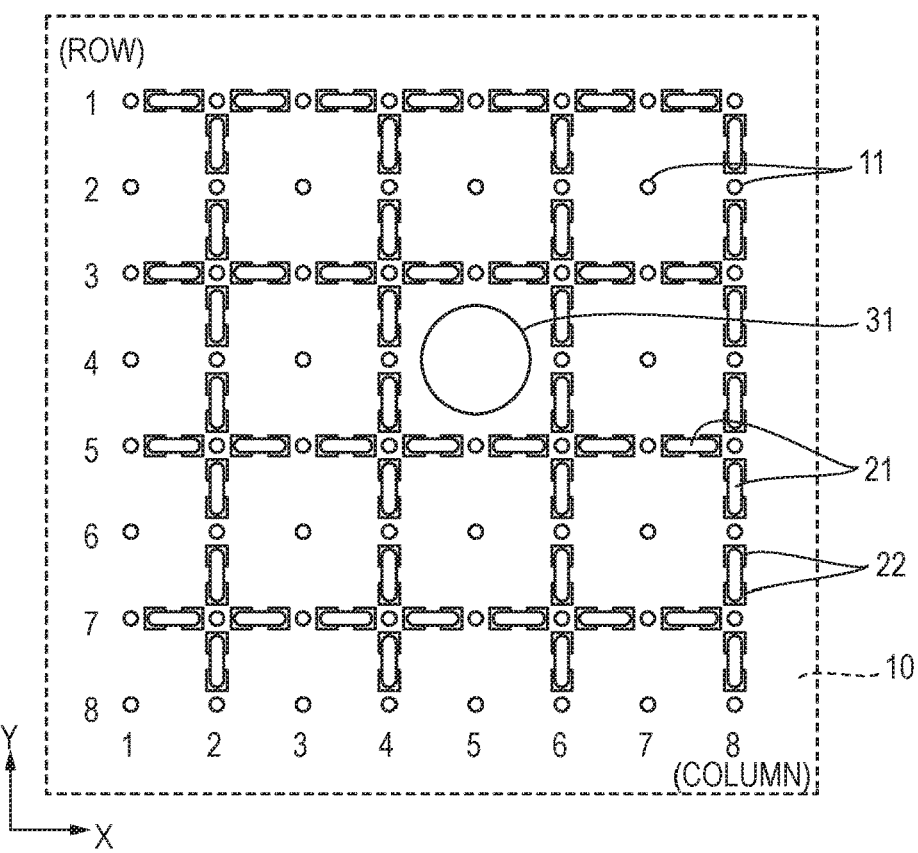
FIG. 4 is a plan view of the measurement target eliminating thin-wire electrodes illustrated in FIG. 3.
Figure 5A:
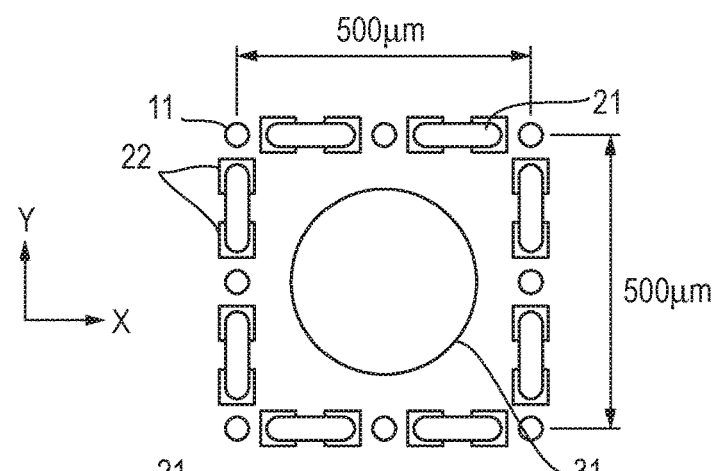
FIG. 5A is an enlarged view of a part of FIG. 4
Figure 5B:
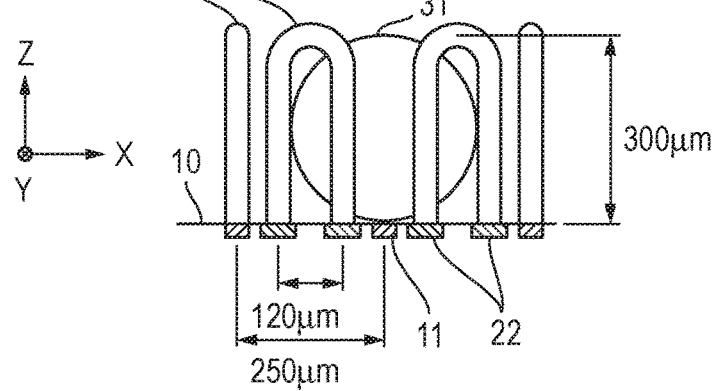
FIG. 5B is a front view corresponding to FIG. 5A.

As illustrated in FIG. 4, the measurement target eliminating thin-wire electrodes 21 were arranged in such a way that each of the measurement target eliminating thin-wire electrodes 21 was positioned between adjacent electrodes in every other row (rows, 1, 3, 5 and 7) of the working electrodes 11 and between adjacent working electrodes 11 in every other column (columns 2, 4, 6 and 8) of the working electrodes 11. In this way, a total of 56 measurement target eliminating thin-wire electrodes 21 were provided on the bottom 10.

It should be noted that such measurement target eliminating thin-wire electrodes 21 can be formed by wire bonding, for example. FIGS. 3, 4, 5A and 5B also illustrate pads 22 for bonding required when the measurement target eliminating thin-wire electrodes 21 are actually mounted.

Figure 6:
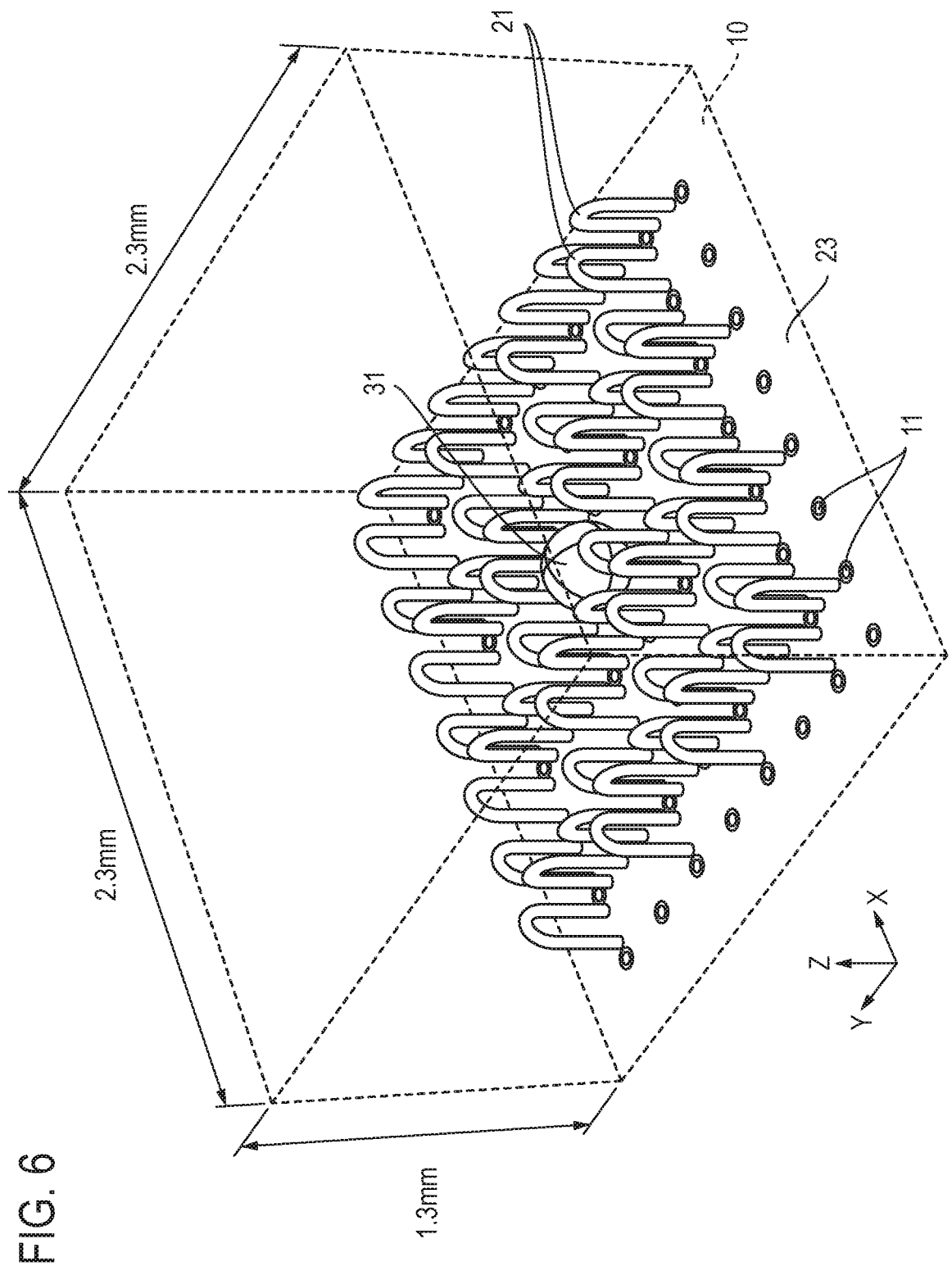
FIG. 6 is a perspective view illustrating an example of measurement target eliminating thin-wire electrodes and a measurement target eliminating bottom electrode in the present invention.

Configuration 2: As illustrated in FIG. 6, a measurement target eliminating bottom electrode 23 that has the same polarity as the working electrodes 11 is disposed at the bottom 10 in addition to the 56 measurement target eliminating thin-wire electrodes 21 of configuration 1. The measurement target eliminating bottom electrode 23 is disposed on the entire bottom 10 with a concentric circular gap of 20 μm around each ϕ40 μm working electrode 11.

Figure 3:
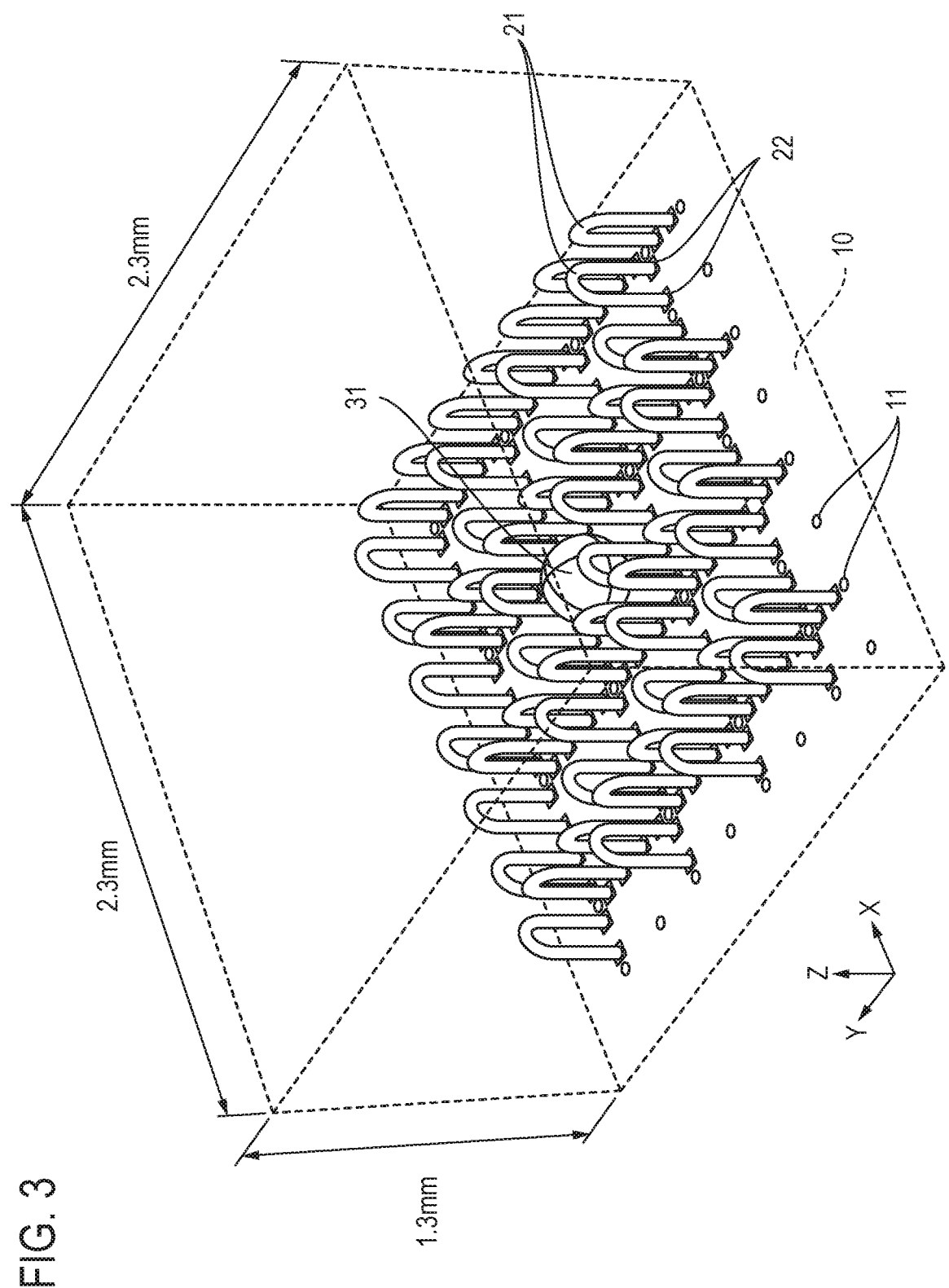
FIG. 3 is a perspective view of an example of measurement target eliminating thin-wire electrodes in the present invention.

It should be noted that this configuration does not require the pad 22 depicted in FIG. 3 and inverted U-shaped measurement target eliminating thin-wire electrode 21 can be mounted by joining (bonding) both ends of the measurement target eliminating thin-wire electrode 21 to the measurement target eliminating bottom electrode 23.

As described above, the measurement target eliminating electrodes in configuration 1 consisted of the measurement target eliminating thin-wire electrodes 21 and the measurement target eliminating electrodes in configuration 2 consisted of the measurement target eliminating thin-wire electrodes 21 and the measurement target eliminating bottom electrode 23.

Voltage application to the measurement target eliminating electrodes was reproduced by setting analytic boundary conditions so that the PAP concentration at the time of voltage application became zero as with the working electrodes.

Figure 7:
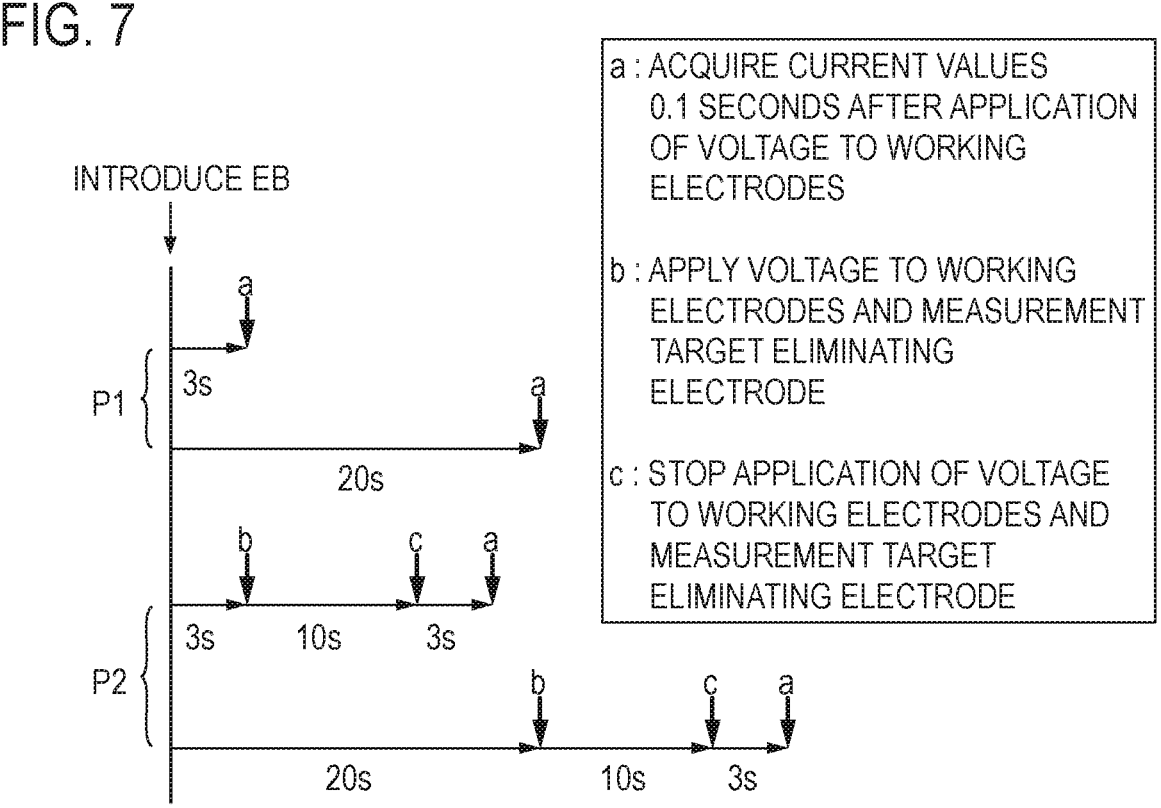
FIG. 7 is a chart illustrating a measurement process of electrochemical measurement according to the present invention together with a conventional measurement process.

P1 in FIG. 7 illustrates a process of the calculation results illustrated in FIG. 2 described above and P2 in FIG. 7 illustrates a process including the measurement target elimination step using the measurement target eliminating electrodes, i.e. a process of the electrochemical measurement method according to the present invention.

It was assumed that the measurement target elimination step (PAP concentration distribution elimination step) was performed for 10 seconds by applying an eliminating voltage of the same polarity as a measuring voltage to the working electrodes and the measurement target eliminating electrodes in a state 3 seconds and 20 seconds after the start of an enzymatic reaction, then the application of the eliminating voltage was stopped and the measurement target diffusion step of causing an enzymatic reaction again for 3 seconds and diffusing a new measurement target was performed, thereafter the electrochemical measurement step was performed to apply the measuring voltage to the working electrodes, and current values 0.1 seconds after were calculated.

Figure 8:
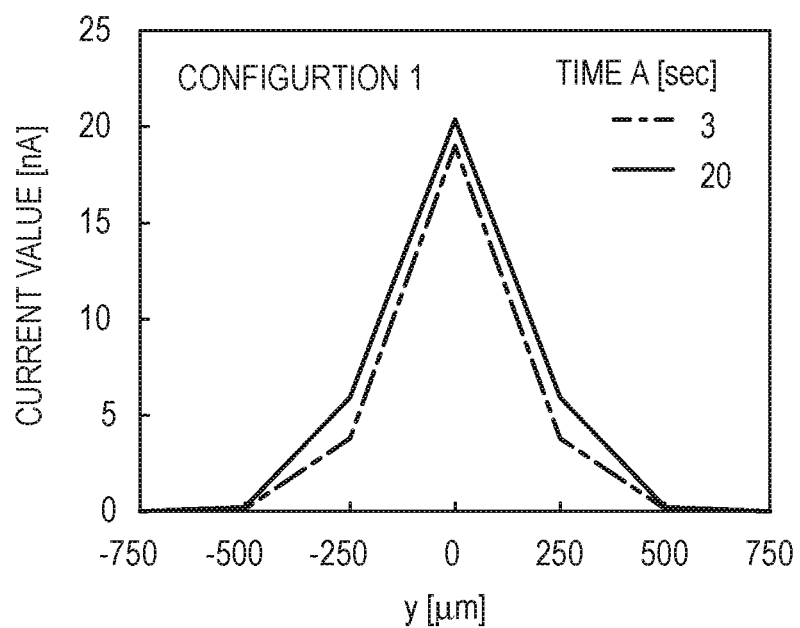
FIG. 8 is a graph illustrating current values calculated by performing a measurement target elimination step using the measurement target eliminating thin-wire electrodes illustrated in FIG. 3.
Figure 9:
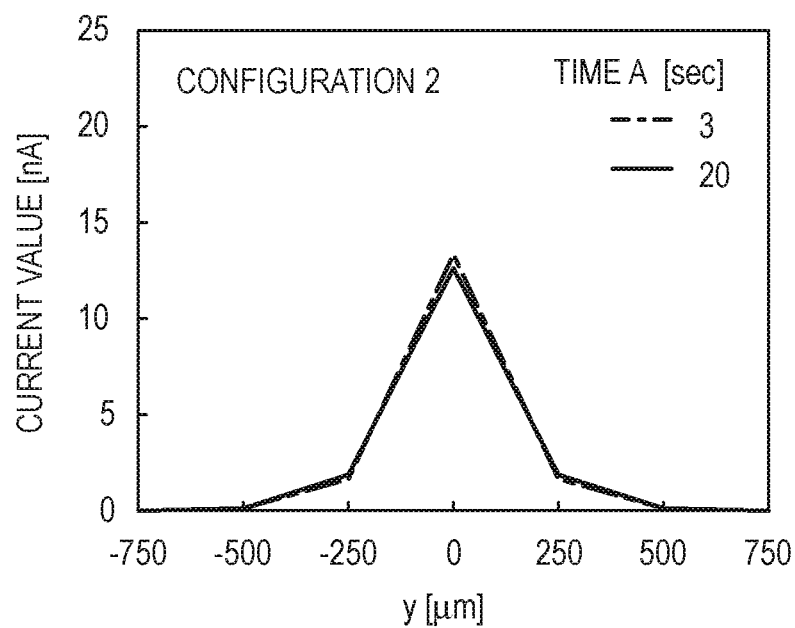
FIG. 9 is a graph illustrating current values calculated by performing the measurement target elimination step using the measurement target eliminating thin-wire electrodes and the measurement target eliminating bottom electrode illustrated in FIG. 6.

FIGS. 8 and 9 illustrate calculated current values for the measurement target eliminating electrodes in configuration 1 and configuration 2, respectively.

Since the reaction (production and diffusion of the measurement target . . . the measurement target diffusion step) after the measurement target elimination step is invariable regardless of whether the period of time before the measurement target elimination step is 3 seconds or 20 seconds, it is desirable that the results for both of the cases where the periods of time before the measurement target elimination step are 3 seconds and 20 seconds be identical. The results for 3 seconds and 20 seconds for configurations 1 and 2 are more sufficiently close to each other than the results illustrated in FIG. 2.

When there is convection in an electrolytic solution, for example, the flow of the electrolytic solution can disturb the PAP concentration distribution formed by an EB and can influence the measurement. Regarding this, results of calculation of effects of the electrochemical measurement method according to the present invention in the case where there is convection in an electrolytic solution will be described. The configuration of the measurement target eliminating electrodes was identical to configuration 2.

Calculations were performed for the following three cases (cases 1 to 3).

Case 1: Current values 0.1 seconds after voltage application where the time from the start of an enzymatic reaction to voltage application is 10 seconds Case 2: Current values 0.1 seconds after voltage application where the time from the start of an enzymatic reaction to the voltage application is 10 seconds and there is convection with a velocity of 50 μm/s in the direction parallel to the array of working electrodes (the Y direction) at the start of the enzymatic reaction Case 3: Current values 0.1 seconds after voltage application where there is convection with a velocity of 50 μm/s in the direction parallel to the array of working electrodes (the Y direction) at the start of an enzymatic reaction, the measurement target elimination step is performed for 10 seconds using the working electrodes and the measurement target eliminating electrodes having the same polarity as the working electrodes after 10 seconds convection, then the application of the eliminating voltage is stopped, an enzymatic reaction is caused again, the measurement target diffusion step is performed for 10 seconds, and then the voltage is applied to the working electrodes.

Figure 10:
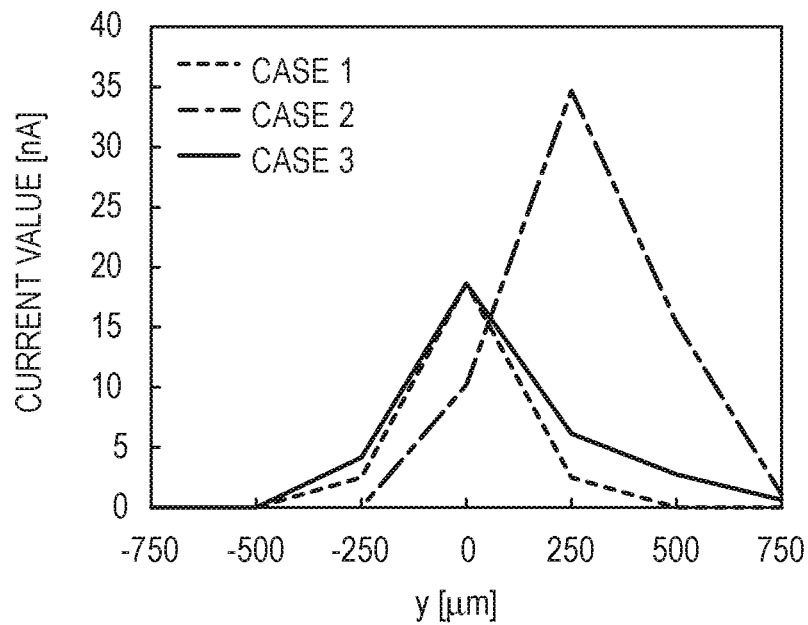
FIG. 10 is a graph illustrating a difference between current values calculated with and without performing the measurement target elimination step in the case where there is convection.

FIG. 10 illustrates results of the calculations of current values in cases 1 to 3. It can be seen that when the measurement target elimination step is not performed, the results are distorted by convection as in case 2 and the peak current value is at a position deviated from where the peak should be (the position in which the EB is located) whereas in case 3 in which the measurement target elimination step is performed, a current value close to the current value in case 1 which should be acquired can be acquired, thus influences of convection and liquid fluctuations can be eliminated.

The results of the numerical analysis performed have been described above. By performing the measurement target elimination step as described above in electrochemical measurement in which working electrodes that supply or receive electrons to or from a measurement target to cause an oxidation-reduction reaction and a counter electrode connected to the working electrodes through an external power source are provided in an electrolytic solution containing the measurement target and a measuring voltage is applied between the working electrodes and the counter electrode to measure a current flowing between the working electrodes and the counter electrode in proportion to the amount of the measurement target, the measurement target that exists at least in a range in the electrolytic solution that influences the measurement is perfectly eliminated by being oxidized or reduced and the process of measurement target production and diffusion thereof is initialized and the state in the electrolytic solution is reset. Accordingly, conditions for production and diffusion of the measurement target can be made uniform among a plurality of repetitions of measurement and among a plurality of samples measured at a time, that is, measurement conditions can be made uniform, by controlling and keeping the duration of the subsequent measurement target diffusion step constant.

Further, by performing the measurement target elimination step in this way, influences of liquid fluctuations and convection of electrolytic solution and the like can be avoided and, in addition, measurement can be performed at a timing desired by a measurer after introduction of samples (biological specimens) that produce a measurement target into the electrolytic solution.

Note that while the measurement target elimination step is performed by applying an eliminating voltage to both of the measurement target eliminating electrodes and working electrodes in the method described above, the measurement target elimination step may be performed by applying the eliminating voltage only to the measurement target eliminating electrodes, for example.

Figure 11:
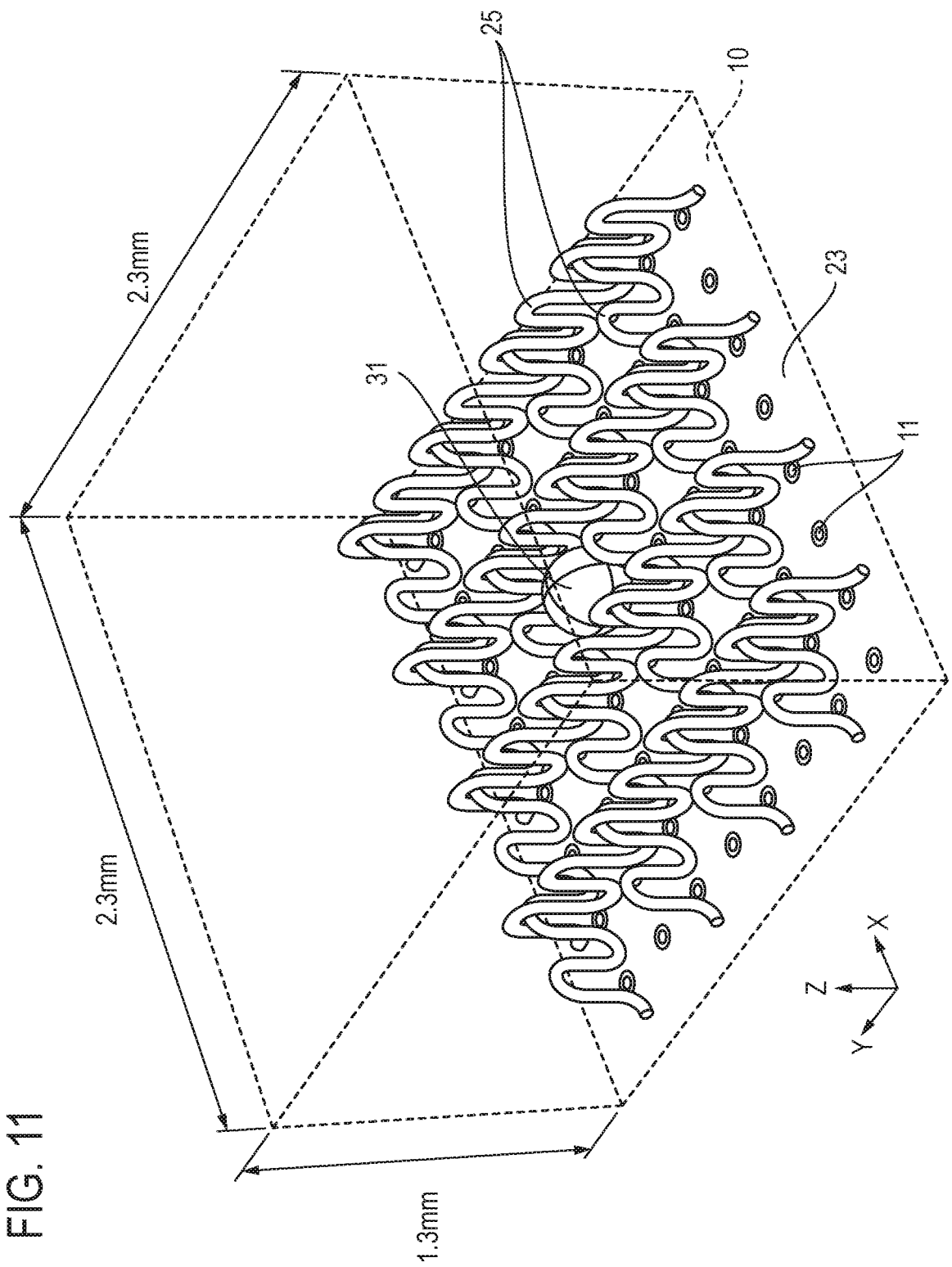
FIG. 11 is a perspective view illustrating another example of measurement target eliminating thin-wire electrodes in the present invention.

While measurement target eliminating thin-wire electrodes 21 are inverted U-shaped and many independent inverted U-shaped measurement target eliminating thin-wire electrodes 21 are arranged in the examples described above, the measurement target eliminating thin-wire electrodes that have a shape and configuration as illustrated in FIG. 11 may be used.

Measurement target eliminating thin-wire electrodes 25 in FIG. 11 have a waved shape in which the shape of the letter U and the shape of inverted U are repeated, in other words, have a configuration in which adjacent ones in the array illustrated in FIGS. 3 and 6 are interconnected through thin wire (by extending thin wires).

The measurement target eliminating thin-wire electrodes 25 are arranged in the same rows and columns as the arrangement of the measurement target eliminating thin-wire electrodes 21 described above, with respect to an array of working electrodes 11. Specifically, the measurement target eliminating thin-wire electrodes 25 are arranged in such a way that four measurement target eliminating thin-wire electrodes 25 that extend in the X direction and four measurement target eliminating thin-wire electrodes 25 that extend in the Y direction intersect each other.

A measurement target eliminating bottom electrode 23 is disposed at the bottom 10, the measurement target eliminating thin-wire electrodes 25 are provided in such a way that the center of the U-shape of the measurement target eliminating thin-wire electrode 25 is located between adjacent working electrodes 11, the center of the inverted U-shape is positioned above a working electrode 11, and the center of the U-shape that contacts the measurement target eliminating bottom electrode 23 is joined (bonded) to the measurement target eliminating bottom electrode 23.

It should be noted that the repetition pitch of waves of the measurement target eliminating thin-wire electrodes 25 is not limited to this example, and for example, may be increased. Accordingly adjacent inverted U-shapes may be bonded at two points instead of at one point. Further, while, in FIG. 11, the measurement target eliminating thin-wire electrodes 25 that are orthogonal to each other intersect above the bottom 10 (above the measurement target eliminating bottom electrode 23), the measurement target eliminating thin-wire electrodes 25 may intersect on the bottom 10.

Figure 12:
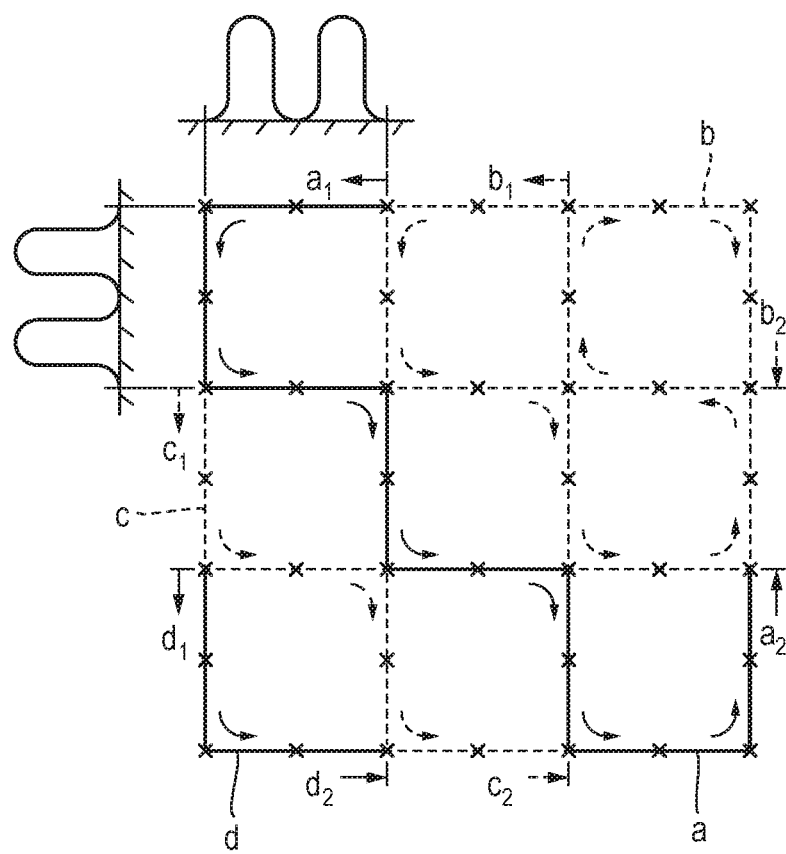
FIG. 12 is a diagram for explaining an example of successive formation of measurement target eliminating thin-wire electrodes.

On the other hand, wavelike measurement target eliminating thin-wire electrodes as described above may be formed in two orthogonal directions without intersections. FIG. 12 schematically illustrates an example of such formation and depicts wavelike measurement target eliminating thin-wire electrodes formed to make a grid pattern of four rows and four columns.

In FIG. 12, cross marks indicate wire bonding positions and arrows indicate the direction in which wires extend (=the order of bonding). In this example,
  wire is extended from $a_1$ to $a_2$ along the path indicated by solid line "a" and bonded.
  wire is extended from $b_1$ to $b_2$ along the path indicated by dashed line "b" and bonded,
  wire is extended from $c_1$ to $c_2$ along the path indicated by dashed line "c" and bonded, and
  wire is extended from $d_1$ to $d_2$ along the path indicated by solid line "d" and bonded. By extending wire in this way, wavelike measurement target eliminating thin-wire electrodes can be formed without intersections.

A configuration of an electrochemical measurement apparatus according to the present invention will be described next.

Figure 13:
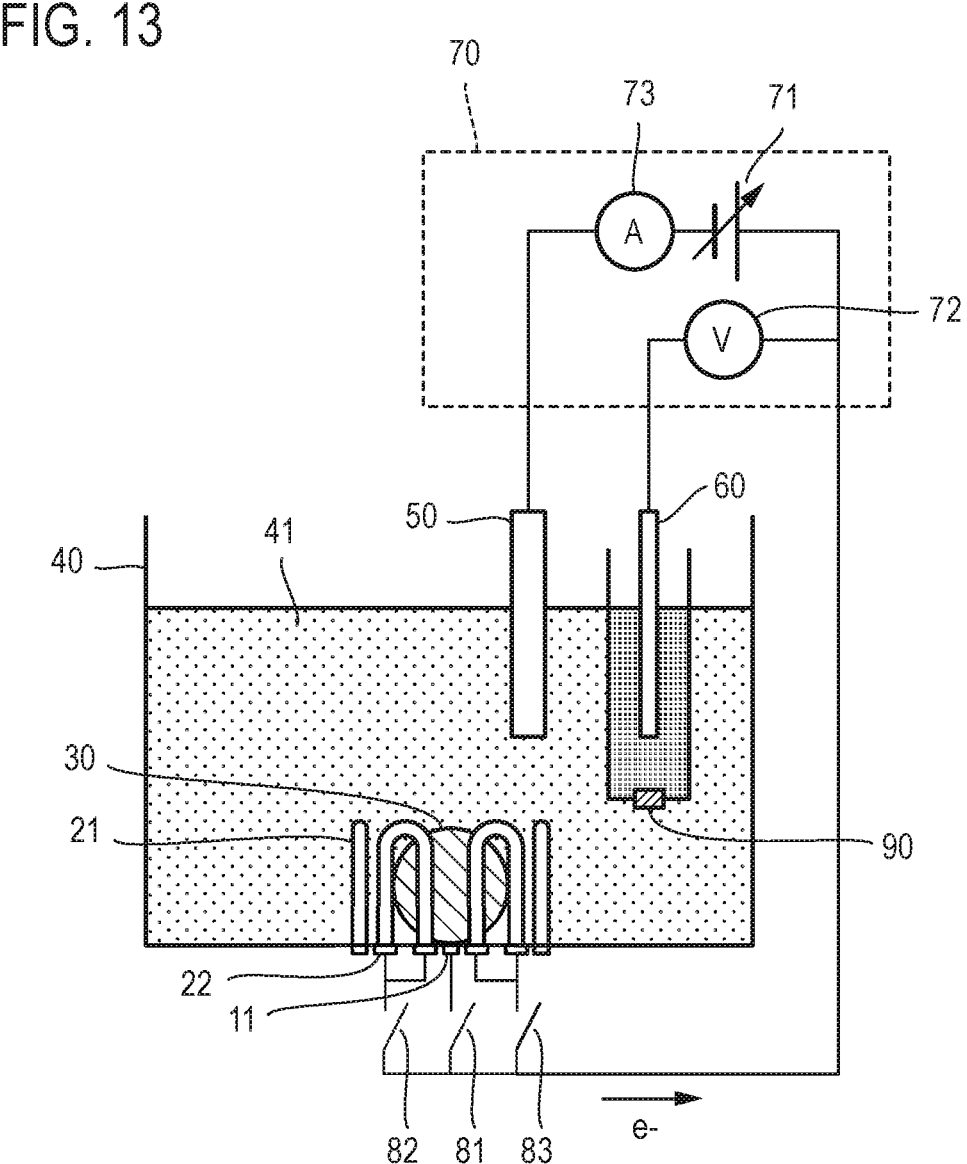
FIG. 13 is a diagram for explaining a configuration of one example embodiment of an electrochemical measurement apparatus according to the present invention.

FIG. 13 schematically illustrates a configuration of the electrochemical measurement apparatus. The electrochemical measurement apparatus includes an electrolytic solution well 40 configured to contain an electrolytic solution 41 and a biological specimen 30 that produces a measurement target in the electrolytic solution 41. A working electrode 11, measurement target eliminating thin-wire electrodes 21, a counter electrode 50 and a reference electrode 60 are provided in the electrolytic solution well 40. While the working electrode 11 and the measurement target eliminating thin-wire electrodes 21 are schematically depicted in FIG. 13, many working electrodes 11 are arranged in an array with a predetermined pitch as described previously and the measurement target eliminating thin-wire electrodes 21 have the configuration illustrated in FIG. 3. It should be noted that a configuration may also include a measurement target eliminating bottom electrode 23 and the measurement target eliminating thin-wire electrodes 21 may be replaced with the measurement target eliminating thin-wire electrodes 25 illustrated in FIG. 11. Reference numeral 90 in FIG. 13 indicates a salt bridge.

The working electrode 11, the measurement target eliminating thin-wire electrodes 21, the counter electrode 50, and the reference electrode 60 in this example are connected to a potentiostat 70 as illustrated in FIG. 13. The potentiostat 70 is configured to include a variable power source 71, a voltmeter 72 and an ammeter 73. A measuring voltage is applied between the working electrode 11 and the counter electrode 50 by the potentiostat 70 and an interelectrode current that flows between the working electrode 11 and the counter electrode 50 in proportion to the amount of a measurement target is measured by the potentiostat 70.

Further, an eliminating voltage that has the same polarity as the measuring voltage is applied between the measurement target eliminating thin-wire electrodes 21 and the counter electrode 50 by the potentiostat 70 while the measuring voltage is not being applied between the working electrode 11 and the counter electrode 50. Application of the measuring voltage to the working electrode 11 is accomplished by turning on a switch 81 and turning off switches 82 and 83; application of the eliminating voltage to the measurement target eliminating thin-wire electrodes 21 is accomplished by turning on the switches 82 and 83 and turning off the switch 81. Note that the eliminating voltage may also be applied to the working electrode 11 by turning on the switch 81.

While the eliminating voltage is applied from the potentiostat 70 to the measurement target eliminating thin-wire electrodes 21 in FIG. 13, application of the eliminating voltage is not so limited; the eliminating voltage may be applied using a power source separate from the potentiostat 70.

Figure 14A:
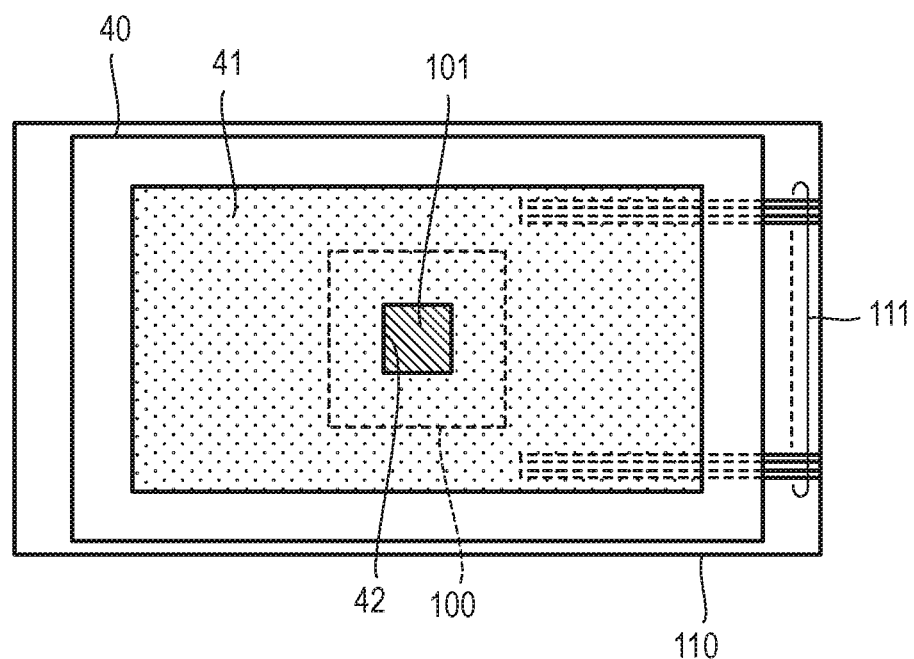
FIG. 14A is a plan view illustrating one example embodiment of a transducer according to the present invention and FIG. 14B is a cross-sectional view of the transducer illustrated in FIG. 14A.
Figure 14B:
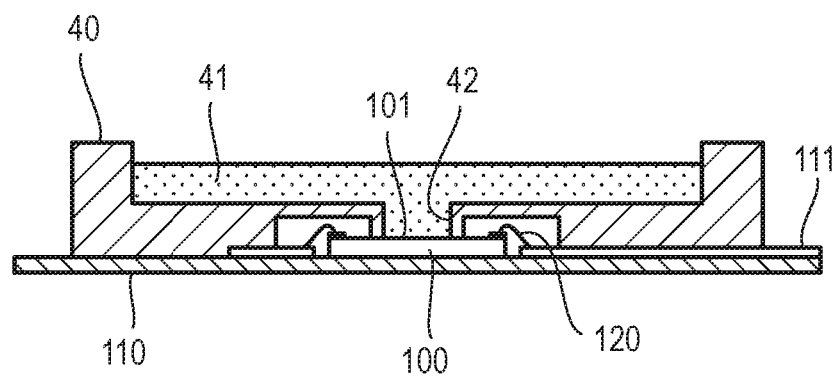
Figure 15:
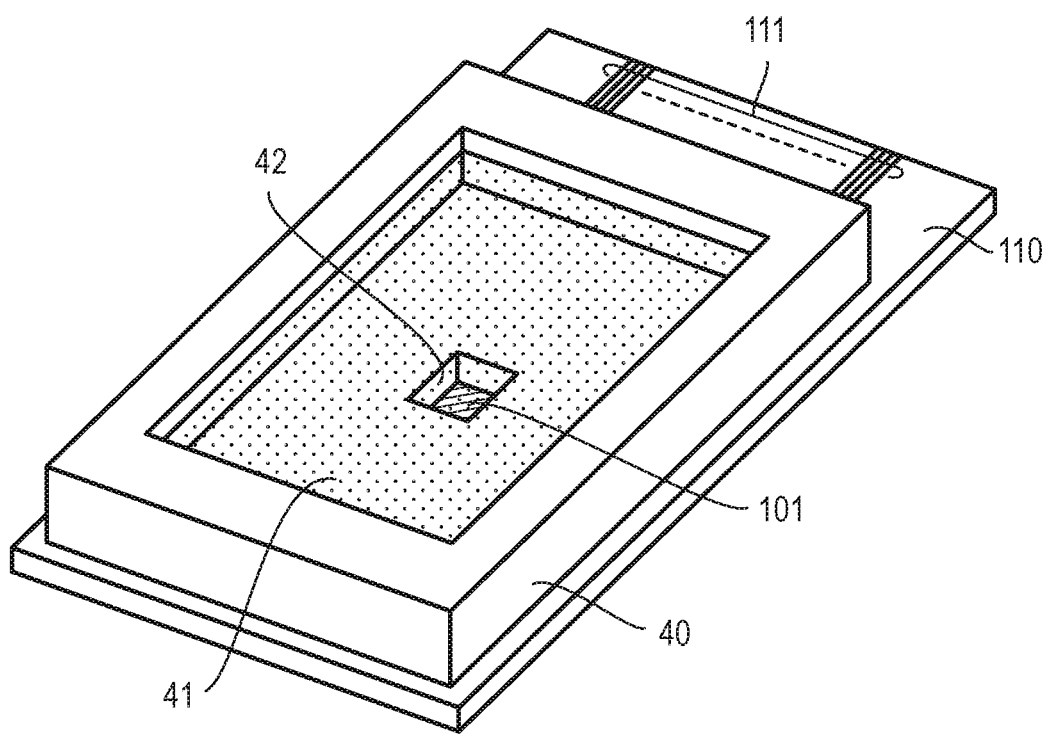
FIG. 15 is a perspective view of the transducer illustrated in FIG. 14A.

A configuration of a transducer according to the present invention that is used for electrochemical measurement of a measurement target produced from a biological specimen will be described next with reference to FIGS. 14A, 14B and 15.

The transducer is called Bio-LSI chip, in which an electrolytic solution well 40 that can contain an electrolytic solution 41 and a biological specimen immersed in the electrolytic solution 41 is mounted on an LSI chip 100. A hole 42 is formed in the center of the electrolytic solution well 40 and the LSI chip 100 is disposed on the bottom end of the hole 42 in such a way that the LSI chip 100 covers the hole 42.

The LSI chip 100 and the electrolytic solution well 40 are mounted and fixed on a substrate 110 and a pattern 111 of many conductors for connection with an external device that controls the transducer is formed on the substrate 110. Reference numeral 120 in FIG. 14B indicates bonding wires that interconnect the LSI chip 100 and the pattern 111 of conductors.

A sensor region 101 is configured on the top surface of the LSI chip 100. In FIG. 14A, the sensor region 101 is indicated by hatching and is defined in the position of the hole 42 in the bottom of the electrolytic solution well 40. While details are omitted from the figure, 20×20=400 working electrodes (first electrodes) of ϕ40 μm are formed in an array with a pitch of 250 μm in the sensor region 101 in this example. Further, measurement target eliminating thin-wire electrodes (second electrodes) are formed on the sensor region 101 each of which is made of thin wire stretched in a shape extending from one point in the sensor region 101 upward into space in the electrolytic solution well 40 and back to another point in the sensor region 101. The measurement target eliminating thin-wire electrodes have, for example, the configuration of the measurement target eliminating thin-wire electrodes 21 described previously and illustrated in FIG. 3.

A configuration may be employed in which a measurement target eliminating bottom electrode (third electrode) is formed in the entire sensor region 101, in addition to measurement target eliminating thin-wire electrodes (second electrodes), in such a way that the measurement target eliminating bottom electrode is located around working electrodes (first electrodes). The transducer in this case may have the configuration of the measurement target eliminating thin-wire electrodes 21 and the measurement target eliminating bottom electrode 23 described previously and illustrated in FIG. 6 or may have the configuration of the measurement target eliminating thin-wire electrodes 25 and the measurement target eliminating bottom electrode 23 described previously and illustrated in FIG. 11.

The LSI chip 100 includes functions such as the function of applying a voltage to each of the working electrodes and the measurement target eliminating electrodes, the function of detecting a reaction at each working electrode as a current value and amplifying the current value, and the function of switching.

While electrode pads of LSI chips in general are made of an Al alloy containing Cu, the working electrodes, the measurement target eliminating bottom electrode located in the sensor region 101 and, if the measurement target eliminating bottom electrode is not provided, pads for bonding the measurement target eliminating thin-wire electrodes, are formed by plating an Al alloy with any of Ti/Pt, Ti/Pt/Au, and Cr/Au, in this example. Au wires are preferably used as thin wires constituting the measurement target eliminating thin-wire electrodes.

Note that a counter electrode and a reference electrode are provided as components separate from the transducer and are placed in the electrolytic solution 41 when measurement is performed (at the point of use).

What is claimed is:

1. An electrochemical measurement method using an electrochemical measurement apparatus that includes: an electrolytic solution well storing an electrolytic solution; a work electrode located on a bottom of the electrolytic solution well; a counter electrode located in the electrolytic solution well; a specimen contained in the electrolytic solution and generating a target substance; and a thin-wire elimination electrode having two ends which are bonded to a pad or which are bonded to a bottom electrode located on the bottom of the electrolytic solution well, the method comprising:

applying an elimination voltage between the thin-wire elimination electrode and the counter electrode to eliminate the target substance by oxidizing or reducing the target substance;

diffusing the target substance by stopping the applying of the elimination voltage; and after the diffusing of the target substance, applying a measurement voltage, which has a same polarity as the elimination voltage, between the work electrode and the counter electrode to measure a current that flows between the work electrode and the counter electrode in response to an amount of the target substance diffused.

2. The electrochemical measurement method according to claim 1,
wherein during the applying of the elimination voltage, the elimination voltage is concurrently applied between the work electrode and the counter electrode.

3. The electrochemical measurement method according to claim 2, wherein:
the electrochemical measurement apparatus includes the pad, and
the thin-wire elimination electrode has a horseshoe shape and the two ends thereof are bonded to the pad.

4. The electrochemical measurement method according to claim 2,
wherein the electrochemical measurement apparatus includes the bottom electrode which has a flat shape,
the bottom electrode has a void inside which the work electrode is positioned,
the thin-wire elimination electrode has a horseshoe shape and the two ends thereof are bonded to the bottom electrode, and
during the applying of the elimination voltage, the elimination voltage is concurrently applied between the bottom electrode and the counter electrode.

5. The electrochemical measurement method according to claim 2,
wherein the electrochemical measurement apparatus includes the bottom electrode which has a flat shape,
the bottom electrode has a void inside which the work electrode is positioned, and
the thin-wire elimination electrode has a serpentine shape and is bonded to the bottom electrode at three or more points including the two ends thereof and one point between the two ends.

6. The electrochemical measurement method according to claim 1,
wherein:
the electrochemical measurement apparatus includes the pad, and
the thin-wire elimination electrode has a horseshoe shape and the two ends thereof are bonded to the pad.

7. The electrochemical measurement method according to claim 1,
wherein the electrochemical measurement apparatus includes the bottom electrode which has a flat shape,
the bottom electrode has a void inside which the work electrode is positioned,
the thin-wire elimination electrode has a horseshoe shape and the two ends thereof are bonded to the bottom electrode, and
during the applying of the elimination voltage, the elimination voltage is concurrently applied between the bottom electrode and the counter electrode.

8. The electrochemical measurement method according to claim 1,
wherein the electrochemical measurement apparatus includes the bottom electrode which has a flat shape,
the bottom electrode has a void inside which the work electrode is positioned, and
the thin-wire elimination electrode has a serpentine shape and is bonded to the bottom electrode at three or more points including the two ends thereof and one point between the two ends.

9. An electrochemical measurement apparatus adapted to measure a current between two electrodes in an electrolytic solution, the current being produced by an oxidation or reduction reaction of a target substance generated by a specimen contained in the electrolytic solution, and the oxidation or reduction reaction being caused by applying a measurement voltage between the two electrodes, the apparatus comprising:
an electrolytic solution well to accommodate the electrolytic solution;
the two electrodes, hereafter one, which is located on a bottom of the electrolytic solution well, being referred to as a work electrode and the other being referred to as a counter electrode;
a thin-wire elimination electrode having two ends which are bonded to a pad or which are bonded to a bottom electrode located on the bottom of the electrolytic solution well; and
a power source configured to apply an elimination voltage between the thin-wire elimination electrode and the counter electrode, the elimination voltage having a same polarity as the measurement voltage.

10. The electrochemical measurement apparatus according to claim 9, wherein:
the electrochemical measurement apparatus includes the pad, and
the thin-wire elimination electrode has a horseshoe shape and the two ends thereof are bonded to the pad.

11. The electrochemical measurement apparatus according to claim 9, wherein:
the electrochemical measurement apparatus includes the bottom electrode,
the bottom electrode has a void inside which the work electrode is positioned, and
the thin-wire elimination electrode has a horseshoe shape and the two ends thereof are bonded to the bottom electrode.

12. The electrochemical measurement apparatus according to claim 9, wherein:
the electrochemical measurement apparatus includes the bottom electrode, the bottom electrode has a void inside which the work electrode is positioned, and
the thin-wire elimination electrode has a serpentine shape and is bonded to the bottom electrode at three or more points including the two ends thereof and one point between the two ends.

13. A transducer for electrochemical measurement of a target substance generated by a specimen contained in an electrolytic solution,
the transducer comprising:
a large scale integrated chip;
an electrolytic solution well to accommodate the electrolytic solution, a hole at a bottom of the electrolytic solution well being stopped with a top surface of the large scale integrated chip;
first electrodes arranged in an array and located in a sensor region that is formed on the top surface of the large scale integrated chip, the sensor region facing an inside of the electrolytic solution well;
a pad or a bottom electrode located in the sensor region; and
a second electrode made of a thin wire having two ends which are bonded to the pad or the bottom electrode.

14. The transducer according to claim 13, wherein:
the transducer includes the pad, and
the second electrode has a horseshoe shape and the two ends thereof are bonded to the pad.

15. The transducer according to claim 13, wherein:
the transducer includes the bottom electrode which has an array of voids, each of the first electrodes is positioned in a corresponding one of the voids without contacting the bottom electrode, and the second electrode has a horseshoe shape and the two ends thereof are bonded to the bottom electrode.

16. The transducer according to claim 13, wherein:

the transducer includes the bottom electrode which has an array of voids, each of the first electrodes is positioned in a corresponding one of the voids without contacting the bottom electrode, and the second electrode has a serpentine shape and is bonded to the bottom electrode at three or more points including the two ends thereof and one point between the two ends.

* * * * *